United States Patent [19]
McAfee

[11] Patent Number: 5,569,290
[45] Date of Patent: Oct. 29, 1996

[54] METHOD OF AND APPARATUS FOR LAPAROSCOPIC OR ENDOSCOPIC SPINAL SURGERY USING AN UNSEALED ANTERIORLY INSERTED TRANSPARENT TROCHAR

[75] Inventor: Paul C. McAfee, 621 E. Belfast Rd., Sparks, Md. 21152

[73] Assignee: Paul C. McAfee, Towson, Md.

[21] Appl. No.: 380,393

[22] Filed: Jan. 30, 1995

[51] Int. Cl.⁶ .................................................. A61B 17/34
[52] U.S. Cl. ........................... 606/185; 606/179; 604/164
[58] Field of Search .................................. 606/185, 179; 604/164, 178, 174

[56] References Cited

U.S. PATENT DOCUMENTS

| | | |
|---|---|---|
| 1,292,998 | 2/1919 | Bell . |
| 2,243,718 | 5/1941 | Moreira ..................................... 128/83 |
| 3,039,468 | 6/1962 | Price ........................................ 128/347 |
| 3,750,667 | 8/1973 | Pshenichny et al. .................... 128/215 |
| 3,789,852 | 2/1974 | Kim et al. ............................... 128/347 |
| 4,493,707 | 1/1985 | Ishihara ................................... 604/164 |
| 4,545,374 | 10/1985 | Jacobson ............................. 128/303 R |
| 4,608,965 | 9/1986 | Anspach, Jr. et al. ...................... 128/4 |
| 4,633,860 | 1/1987 | Korth et al. ............................. 128/305 |
| 4,774,948 | 10/1988 | Markham ............................. 128/329 R |
| 4,785,826 | 11/1988 | Ward ....................................... 128/754 |
| 4,819,620 | 4/1989 | Okutsu ....................................... 128/4 |
| 4,863,430 | 9/1989 | Klyce et al. ............................. 604/164 |
| 4,911,173 | 3/1990 | Terwilliger ........................ 128/662.06 |
| 5,122,122 | 6/1992 | Allgood .................................. 604/174 |
| 5,139,487 | 8/1992 | Baber ...................................... 604/165 |
| 5,273,026 | 12/1993 | Wilk ......................................... 128/20 |
| 5,279,575 | 1/1994 | Sugarbaker ............................. 604/174 |
| 5,295,952 | 3/1994 | Pietrafitta .................................. 604/1 |
| 5,385,572 | 1/1995 | Nobles et al. .......................... 606/185 |

OTHER PUBLICATIONS

U.S.A. Today newspaper article, Oct. 18, 1993 by Mike Snider entitled "TV–aided Back Surgery Cuts Hospital Stay".

*Primary Examiner*—Michael Powell Buiz
*Assistant Examiner*—Mark S. Leonardo
*Attorney, Agent, or Firm*—Armstrong, Westerman, Hattori, McLeland & Naughton

[57] ABSTRACT

A method of and apparatus for performing endoscopic or laparoscopic surgery on a patient's spine is provided. The apparatus includes a trochar which is specifically design for spinal applications. The trochar includes of a first transparent tubular member of a predetermined diameter and a second transparent tubular member of a slightly larger diameter than the first transparent tubular member. The first transparent tubular member fits slidingly within the second transparent tubular member in a telescoping manner. The first transparent tubular member has two ends: an end for remaining in side-to-side contact with said second tubular member and a free end which has an attached metal fitting with serrated teeth for anchoring in the patient's vertebrae when the trochar is inserted through a incision made in the patient's abdomen or chest. The trochar also includes a collar and set screw arrangement. The collar is made up of a short tubular portion having a flanged end. The flanged end is annularly shaped and protrudes approximately perpendicularly outwardly from the short tubular portion of the collar. The short tubular portion of the collar has a threaded aperture therethrough. The threaded aperture threadingly mates with a set screw which when turned far enough counterclockwise prevents the first tube from telescoping within the second tube. Additionally, the collar and set screw arrangement also functions to stabilize the trochar in an approximately upright position at an angle to the patient's body.

19 Claims, 3 Drawing Sheets

METHOD OF AND APPARATUS FOR LAPAROSCOPIC OR ENDOSCOPIC SPINAL SURGERY USING AN UNSEALED ANTERIORLY INSERTED TRANSPARENT TROCHAR

FIELD OF THE INVENTION

The present invention relates generally to instruments and procedures for performing spinal surgeries and, more particularly, to a method of and apparatus for performing laparoscopic or endoscopic surgical procedures on a patient's spine using a trochar specifically designed for spinal applications which includes a dually functioning flanged collar and set screw arrangement slidably mounted on the outer of two transparent telescoping inner and outer tubular members forming an unsealed, open-air passageway for insertion of surgical instruments therethrough after the trochar is inserted through an incision made in the patient's abdomen or chest so that the free end of the inner tubular member having a metal fitting with serrated teeth is anchored into a vertebrae of the patient's spine for end organ docking.

BACKGROUND OF THE INVENTION

Currently, instruments called trochars are well known within the medical sciences. Indeed, surgeons today often use trochars to perform a variety of medical and surgical procedures. A medical dictionary defines a trochar as a sharp pointed surgical instrument for use with a cannula in order to puncture a body cavity for fluid aspiration. However, trochars may also be used for paracentesis, i.e., as the means providing a passageway into a body cavity.

When used for paracentesis, a typical trochar usually includes two tubular members. A first tubular member has a slightly larger diameter than a second tubular member. This allows the second tubular member which is of a slightly smaller diameter to be placed to fit within the first tubular member of a slightly larger diameter.

The two tubular members when positioned one within the other may be moved relative to each other in a telescoping manner. When telescoped, each tubular member has one free end and one end remaining in side-to-side adjacent contact with the other tubular member.

For use in a surgical procedure, the free end of the inner tubular member of the trochar is then usually inserted into a body cavity through an incision made in the patient's body. The trochar is used as a passageway through which specially designed, long-necked surgical instruments can be inserted in order to perform a surgical procedure within the body cavity.

Although trochars have previously been used to perform surgical procedures on a patient's spine, spinal surgeries using trochars have not been the favored way of performing surgery on the spine. This is due to the following complications of spine surgeries using trochars.

A first complication stems from the fact that a typical spinal trochar to date has usually had two telescoping tubes made of metal. Metal seems to be the material of choice because it can withstand the high temperature necessary to sterilize the trochar. However, metal trochars are disadvantageous because they do not offer the surgeon any view of the area on which he or she is performing the surgery.

To date, surgeons using metal trochars have had to depend on x-rays in order to view what is going on inside of the trochar. Continued exposure to X-rays can be harmful to the patient. Therefore, the patient must be protected during surgery from the continual exposure to harmful x-rays by use of a heavy leaded gown. The leaded gown can add further difficulties to the surgery, particularly, if the patient's position must be moved during the surgical procedure in order to access different bodily organs, bones or other internal parts.

Additionally, the use of x-rays is a time-consuming and imprecise manner of performing surgery on a patient's spine, especially since the spine is such a delicate and sensitive area of the body. Indeed, the spine protects the spinal chord which runs along the outside of the vertebrae nearer the skin on the patient's back. The spinal chord houses various nerves which allow the patient to walk and perform other functions. Because the spinal chord runs along the patient's back on the outside of the spine it is safest to perform spinal surgeries anteriorly rather than posteriorly in order not to interfere with the spinal chord in any way.

Another complication with conventional spinal surgical procedures using trochars is that to date these surgeries have always been performed in such a manner so as to require insufflation. Insufflation is defined as the act of blowing a powder, vapor, gas, or air into a body cavity.

The body cavity through which a trochar must be passed contains carbon dioxide or $CO_2$ gas. To date, surgeons have always felt that the trochar used needs to be sealed against ambient air entering the $CO_2$ filled body cavity. Thus, in order to keep the ambient air in the operating room from entering the body cavity, trochars have been sealed and carbon dioxide gas has been blown into the passageway created by the trochar in order that ambient air not enter the body cavity. However, trying to pass a surgical instrument through a sealed trochar is difficult and time consuming and there is always some amount of leakage.

As noted above there are numerous drawbacks associated with conventional trochars now being used in spinal surgical procedures. Because the present invention is the first trochar specifically designed for spinal surgeries it tends to avoid many of the pitfalls which occur with conventional trochars.

More particularly, the trochar of the present invention was designed for end organ docking which means it goes from the patient's skin and inserts directly into an anchored position in the patient's spine without harming the spine.

To date, few, if any, trochars have been made of a transparent material as is the apparatus of the present invention, mainly because no plexiglass-like material could be found that could be pushed, pulled and twisted through the extrusion process and would not break. The present invention uses an acrylic tubing that can withstand the extrusion process and the high temperatures necessary to sterilize the trochar for surgery.

It would be desirable to have a trochar which allowed the surgeon a more direct view of the area of the patient's spine on which he or she was performing the medical procedure in order to perform the spinal surgery with more precision and accuracy. The apparatus of the present invention allows for better viewing of the area in which the surgeon is performing the surgery by means of a miniaturized video camera placed adjacent to the outer periphery of the trochar's transparent tubular members. The video camera lights the surgical area to be viewed during the course of the surgery and provides video images via a fiberoptic cable to allow the surgeon to view from a monitor the area on which he is operating.

Another disadvantage of conventional spinal surgical trochars used today is that the trochars are typically designed in such a manner that the cylindrical passageway which is created by the trochar for insertion of the surgical instruments must be kept closed and sealed so that the ambient air in the operating room cannot come into contact with the air in the passageway of the trochar in order not to contaminate the conditions in the body cavity into which trochar has been introduced.

With the apparatus of the present invention, the trochar is specifically designed to be open at the instrument insertion end. It is desired to allow the ambient air to flow into and out of the cylindrical passageway created by the trochar between the sterilized conditions in the operating room and the internal cavity of the patient into which the trochar is inserted. It has been found that there is no need to seal the cylindrical passageway of the trochar from the ambient air conditions and thus, there is no need for insufflation. This simplifies the surgical procedure and allows the surgeon to concentrate on the details of the surgery rather than worrying about maintaining the sealed condition of the trochar passageway. However, the trochar of the present invention may be used either with or without the insufflation of gas to perform surgical procedures on the thoracic or the lumbar spine.

An advantage of the method and apparatus of the present invention is that in connecting with the external environment rather than creating an articifially sealed environment, the trochar creates lesser damage and disturbance to the surrounding tissue. This allows patients a faster recuperative period. In fact, tests have shown that patients may be getting out of bed and moving around in a matter of days after surgery with the trochar of the present invention rather than weeks as is required with the conventional surgical apparatus and procedures.

It is an object of the present invention to provide a trochar which is specifically designed for spinal surgery performed through an incision made in the patient's abdomen.

Another object of the present invention is to provide a surgical instrument designed as an end organ trochar so that the trochar goes from an incision made through the patient's skin to be inserted into the patient's spine and anchored by means of sharp prongs or serrated teeth into a spinal bone or vertebrae.

Another object of the present invention is to provide the first trochar which is transparent so that the removal of spinal bones or ligaments can be visualized directly with the aid of a video camera placed adjacent to the outside wall of the transparent trochar.

Another object of the present invention is to provide a trochar for spinal surgery that can be used with or without insufflation, i.e., the act or process of blowing a gaseous vapor into a body cavity or an airway, on the thoracic or lumbar spine.

Another object of the present invention is to provide a trochar for spinal surgery which is open to ambient air without having to be sealed against the entry of air into the passageway into which the surgical instruments are placed.

Another object of the present invention is to reduce blood loss during the operation and pain drugs needed during and after the surgical procedure by means of smaller incisions and less tearing and damage to internal tissue.

Another object of the present invention is to reduce the amount of time the patient must remain in the intensive care unit in the hospital and in the hospital in general.

Another object of the present invention is to provide a surgical instrument which causes the patient to have better post-operative results as previously used equipment.

Another object of the present invention is to get patients back to normal sooner, often within four (4) to six (6) weeks as compared to three (3) months with the prior art procedure.

SUMMARY OF THE INVENTION

The present invention provides a method of and apparatus for performing endoscopic or laparoscopic surgery on a patient's spine through an anterior approach. The apparatus includes a trocar having two telescoping, clear or transparent tubes with a first tube being of a slightly smaller or lesser diameter than a second tube in order for the first tube to fit within the second tube in a slidingly telescoping manner. The apparatus also includes a collar with a set screw arrangement.

The collar is slidingly mounted on and around the outer tube of larger diameter in order to be able to prevent telescoping of the smaller diameter tube within the larger diameter tube by means of tightening the set screw which threadingly mates with an aperture through the side wall of the collar. When the set screw is turned in a clockwise manner, it begins to make the outer larger diameter tube press against the inner smaller diameter tube of the trochar. When the tubes are pressed against each other tightly enough, the inner smaller diameter tube will be prevented from telescoping within the outer larger diameter tube The collar also functions as a stabilizer in that when the trochar is fully inserted into the incision made in the patient's abdomen so that the metal fitting on the end of the inner smaller diameter tube is anchored on a spinal bone, the surgeon will position the collar directly adjacent and resting against the patient's abdomen or chest in order to keep the trochar in as stable of an approximately upright position relative to the patient's body as possible.

The apparatus also includes an anchoring member in the form of a toothed cylindrical metal fitting which is used to anchor the inner, smaller diameter tubular member directly to one of the patient's spinal bone.

The method of the performing a variety of endoscopic or laparoscopic surgical procedures on a patient's spine using the trochar of the present invention includes the method steps of: making a small incision in the patient's abdomen or chest; inserting a trochar which includes a first transparent tube of a predetermined diameter and a second transparent tube of a slightly greater diameter that slidingly accepts the first tube in a telescoping manner through the incision; anchoring a pronged or toothed metal member threadingly placed on one end of the first transparent tube in to one of the patient's spine bones; positioning a set screw and collar arrangement slidingly mounted on the second transparent tube against the patient's body so that a flanged end of said collar arrangement rests against the patient's body in order to stabilize the trochar in an approximately upright position somewhat perpendicular to the patient's body; and tightening a set screw threadingly mounted through the collar arrangement slidingly mounted on the second transparent tube to prevent further telescoping of the first and second transparent tubes during surgery.

The method further includes the step of passing a miniaturized video camera with lens and fiberoptic cable through the incision in order for the camera lens to be positioned adjacent the outer periphery of the first and second transparent telescoping tubes. The method further includes the method step of turning on the miniaturized video camera in order to view an area of the patient's spine to be operated on. The method further includes the method step of transmitting video images of the area of the patient's spine being operated on to assist a surgeon in performing a particular surgical procedure on the patient's spine. The method further includes the method step of inserting a surgical instrument into a passageway created by the first and second transparent telescoping tubes in order to use the instrument to perform a particular part of said surgical procedure on the patient's spine and then removing the surgical instrument from the passageway. The method further includes the method step of removing the trochar from the incision made in the patient's body. The method further includes the method step of suturing the incision made in the patient's abdomen or chest in order to complete the surgical procedure.

BRIEF DESCRIPTION OF THE DRAWING FIGURES

DETAILED DESCRIPTION OF THE INVENTION

Figure 1:
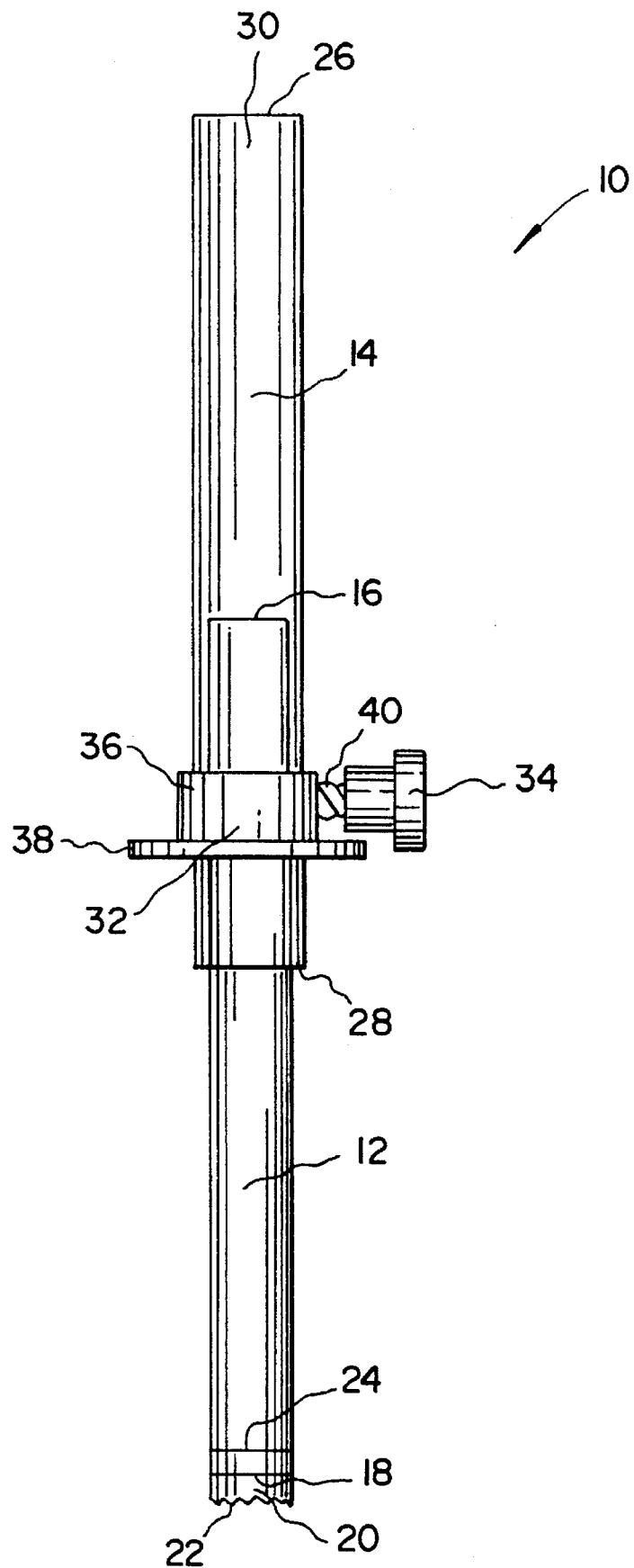
FIG. 1 is a perspective view of the apparatus of the present invention.

The drawing figures depict the method of and apparatus for performing endoscopic or laparoscopic surgery on a patient's spine using an anterior approach. Referring to FIG. 1, the apparatus 10 of the present invention is shown in perspective view. The apparatus 10 is a trochar which includes two transparent tubular members 12, 14 as are shown in more detail in FIGS. 2 and 3.

Figure 2:
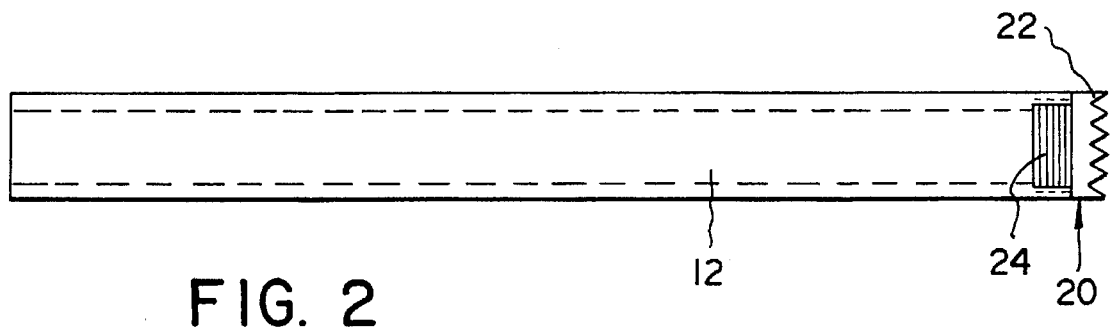
FIGS. 2 is a plan view of the first tubular member or the end organ docking member of the trochar of the present invention.

Referring to FIG. 2, the first or inner tubular member 12 is also called an end organ docking tubular member because it goes all the way from an incision made in the skin to and inserts into the spine. The first or inner tubular member 12 is of a slightly smaller diameter than the second tubular member 14.

In the preferred embodiment of the present invention, the outer diameter of the first or inner tubular member 12 is approximately 0.75 of an inch and the inner diameter is approximately 0.59 of an inch. The walls of the first or inner tubular member are preferably approximately 0.125 of an inch thick.

The first tubular member 12 has two ends 16 and 18. The first end 16 is smoothly rounded in order to be inserted into the second tubular member 14 for telescopingly sliding. The second end 18 of the first tubular member 12 is also smoothly rounded to accept a metallic fitting called a bottom drive bushing 20. The bottom drive bushing 20 has a serrated end 22 and a threaded end 24. The threaded end 24 is screwed into the second end 18 of the first tubular member 12 in order to threadingly mate with the inner periphery 26 of the first or inner tubular member 12.

Figure 5:
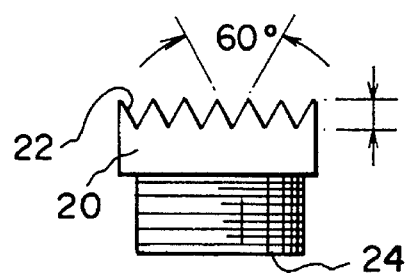
FIG. 5 is a plan view of the bottom drive bushing of the trochar of the present invention.

Referring to FIG. 5, the serrated end 22 has teeth which are preferably approximately 0.25 of an inch long with the entire metal fitting being preferably approximately 0.50 of an inch long. The serrated end 22 is preferred because it helps drive the trochar into the incision made in the patient's abdomen in order to come to rest and anchor into one of the spinal vertebrae.

Figure 3:
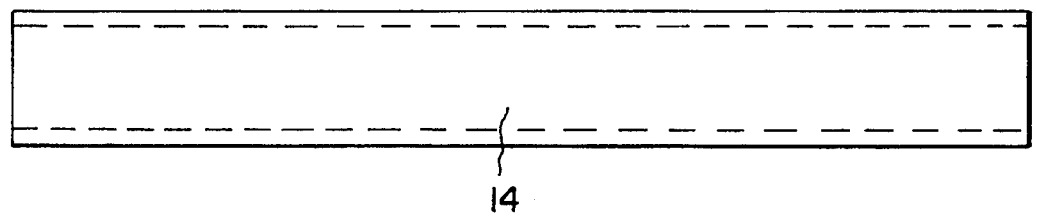
FIG. 3 is a plan view of the second tubular member or the guide shield of the trochar of the present invention.

Referring to FIG. 3, the second or outer tubular member 14 is shown. The second or outer tubular member 14 is also called the guide shield. This is because the first or inner tubular member 12 is inserted into the second or outer tubular member 14 in order to be guided by the second or outer tubular member 14 in its telescoping motion.

The second or outer tubular member also has two ends 26 and 28. Both ends 26, 28 are smoothly rounded with the first end acting as the beginning of the cylindrical passageway 30 into which the surgeon inserts the surgical instruments to perform the surgical procedure on the patient's spine.

In the preferred embodiment of the present invention, the outer diameter of the second or outer tubular member 14 is approximately 1 inch and the inner diameter is approximately 0.76 of an inch. The walls of the second or outer tubular member 14 are preferably approximately 0.125 of an inch thick.

In the preferred embodiment of the invention, the tubular members 12, 14 are each approximately twelve (12) inches long. However, the length of the tubular members 12, 14 is not limiting and the tubular members can be made of any length that is suitable to the purpose for which the trochar 10 is to be used.

The tubes are preferably made of a clear or transparent polycarbonate (PCB) plastic similar to plexi-glass except having glass reinforced Lexan resins in order to bring the performance of the polycarbonate to levels approaching metals. However, any material with suitable properties of transparency and toughness may be used.

Figure 4:
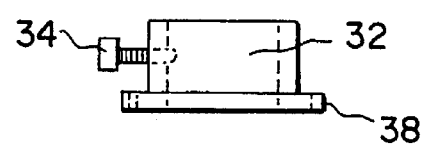
FIG. 4 is a plan view of the collar and set screw arrangement of the trochar of the present invention.

Referring to FIG. 4, a collar 32 and thumb set screw 34 arrangement or the purse string and suture sleeve is shown. The collar 32 is made of metal, preferably steel, and has a tubular portion 36 with an outwardly transverse extending flange 38. The tubular portion 36 of the collar 32 has an inner diameter of approximately 1 inch or slightly larger in order to fit slidingly on and around the second or outer tubular member 14.

At one end of the tubular portion 36 of the collar 32 is a flange 38 which is an annular shaped member protruding approximately perpendicularly outwardly from the tubular portion 36 of the collar 32. The tubular portion 36 of the collar 32 has a threaded aperture 40 therethrough in order to threadingly mate or accept a threaded thumb set screw 34.

The set screw 34 turns in a counterclockwise manner in order to be threaded into the aperture 40 in the tubular portion 36 of the collar 32. When the set screw 34 is turned far enough clockwise, the end 42 of the set screw 34, which is preferably nylon tipped, begins to protrude past the inner peripheral surface 44 of the tubular portion 36 of the collar 32 and pushes against the outer peripheral wall 46 of the second transparent tubular member 14. In so doing, the second transparent tubular member 14 is constricted and tightens about the first transparent tubular member 12.

When the set screw 34 is turned far enough counterclockwise, the first or inner telescoping transparent tubular member 12 is prevented from telescoping within the second transparent tubular member 14. This is necessary because it is not desirable to have the trochar telescoping during the surgical procedure the surgeon is performing on the patient's spine.

The collar 32 itself serves a second function other than preventing the telescoping of the first and second transparent tubular members 12, 14. The collar 32 also acts as a stabilizer. Once the trochar 10 is positioned within the incision made in the patient's abdomen, the flanged end 38 of the collar 32 is positioned so as to rest against the patient's body. In this manner, the collar 32 acts to stabilize the trochar 10 in an upright position, approximately perpendicular to the patient's body. It is important during surgery that the trochar 10 be stable in order for the surgeon to insert surgical instruments through the cylindrical passageway 30 within the trochar 10 to be able to perform various medical procedures on the patient's spine.

A prototype of the trochar 10 of the present invention has been built and tested. The two transparent telescoping tubular members 12, 14 of the trochar 10 were made of a plexiglass-like material such as polycarbonate (PCB) plastic. The polycarbonate was manufactured with a glass reinforced Lexan resin in order to bring the performance to levels approaching metals. This material was chosen because of its transparency, toughness and durability.

Figure 6:
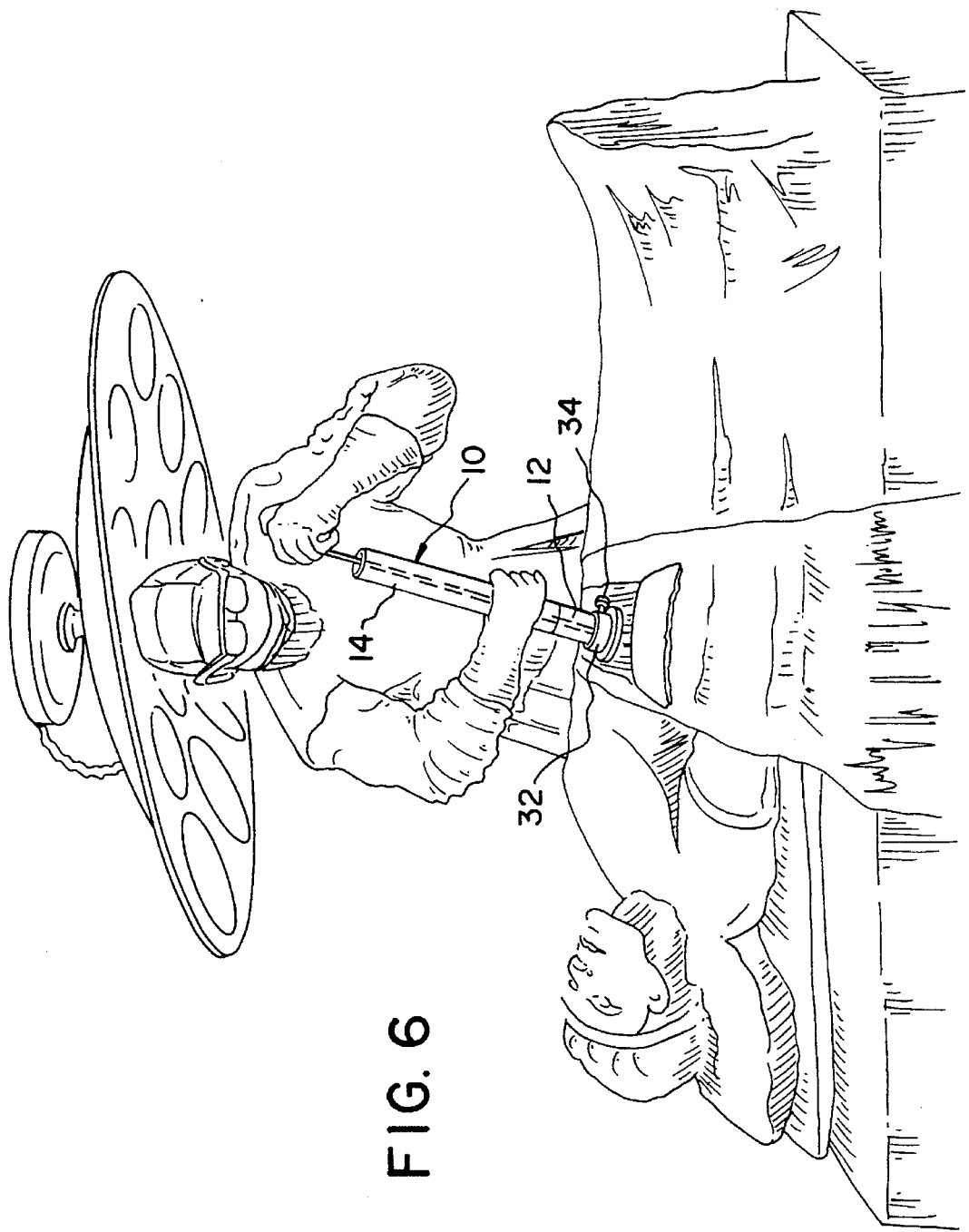
FIG. 6 is a perspective view of a physician performing laparoscopic or endoscopic surgery on a patient's spine using the trochar of the present invention with an anterior approach.

In operation, the trochar of the present invention is used as follows. First, a patient is gotten ready for surgery or prepped and given anesthesia. Referring to FIG. 6, the surgeon then makes an incision in the patient's abdominal or chest cavity. The trochar 10 is inserted through the patient's abdomen or chest and is anchored in one of the spinal bones via the pronged or serrated metal fitting 20 on the second end of the first transparent tubular member 12.

The first and second transparent tubular members 12, 14 are telescoped to an appropriate length for surgery and the collar 32 and set screw 34 arrangement that is slidingly mounted on said second transparent tubular member 14 is positioned against said patient's body so that a flat flanged end 38 of the collar 32 rests against the patient's body in order to stabilize the trochar 10 in an upright position approximately perpendicular to the patient's body. Then, the set screw 34 that is threadingly mounted on the collar 32 slidingly mounted on said second transparent tubular member 14 is turned counterclockwise to be tightened in order to prevent further telescoping of said first and second transparent tubular members 12, 14 during surgery.

A thoracoscope or miniaturized television or video camera 48 with lens 50 and fiberoptic cable 52 is passed through the incision made in the patient's abdomen in order to be placed adjacent the outer peripheral side wall of the first and second telescoping transparent tubular members 12, 14. The thoracoscope or miniaturized television or video camera 48 is turned on in order to light the area of said patient's spine being operated on. A video image of the area of the patient's spine being operated on is transmitted to a screen to assist the surgeon in performing a particular surgical procedure on the patient's spine.

The surgeon is then ready to insert various surgical instruments into the passageway 30 created by the first and second transparent telescoping tubular members 12, 14, in order to perform the appropriate surgical procedures on the patient's spine. Once the surgeon has completed the surgery, the trochar be and miniaturized video camera 48 are removed from the incision made in the patient's abdomen and the incision in the patient's abdomen is sutured in order to complete said surgical procedure and allow the patient to recover and heal.

The present invention has been shown in the drawing figures and described in detail in its preferred embodiment for the purposes of illustration, however, variations and departures can be made therefrom by one of ordinary skill in the art without departing from the spirit and scope of the invention as claimed below.

I claim:

1. An apparatus for use in endoscopic or laparoscopic surgery on a patient's spine comprising:

means for forming a passageway to said patient's spine through an incision made in said patient's abdominal or chest for the insertion of specially designed long-necked surgical instruments therethrough to perform a surgerical procedure on said patient's spine wherein said means forming said passageway includes an inner tubular member of a first diameter and an outer tubular member of a second diameter which is slightly larger than said first diameter in order for said inner tubular member to fit telescopingly within said outer tubular member;

means for dually functioning to prevent telescoping of said inner tubular member within said outer tubular member and to stabilize said means for forming a passageway in a position for use during surgery against movement relative to said patient's spine; and means positioned on an end of said inner tubular member for anchoring said means for forming a passageway to a vertebrae in said patient's spine, wherein said means for anchoring is a tubular metal fitting and wherein said tubular metal fitting has a plurality of serrated teeth on one end and on an opposite end a threaded outer periphery which mates with an inner periphery of said inner tubular member.

2. The apparatus as in claim 1 wherein said serrated teeth are approximately 0.25 inches long and have an approximately 60° angle.

3. The apparatus as in claim 2 wherein said means for dually functioning to prevent telescoping and to stabilize is a collar and set screw arrangement.

4. The apparatus as in claim 3 wherein said collar has a means for slidingly mounting on said outer tubular member.

5. The apparatus as in claim 4 wherein said means for mounting on said outer tubular member is a short metal tube portion having a flanged end such that said flanged end protrudes approximately perpendicularly outwardly from said short metal tube portion.

6. The apparatus as in claim 5 wherein said short metal tube portion has a threaded aperture therethrough which mates with a set screw in order to prevent telescoping of said inner transparent tube within said outer transparent tube.

7. The apparatus as in claim 6 wherein said set screw has a nylon tip in order to tighten said set screw without harming either of said tubular members.

8. The apparatus as in claim 7 wherein said short metal tube portion with said flanged end is made of steel.

9. The apparatus as in claim 8 wherein said inner and outer tubular members are made of a transparent material.

10. The apparatus as in claim 9 wherein said transparent material is a plastic which is resilient enough to be capable being extruded and can withstand the high temperatures necessary for sterilization.

11. The apparatus as in claim 10 wherein said plastic is polycarbonate with glass reinforced Lexan resins in order for said polycarbonate to perform at levels approaching metals.

12. The apparatus as in claim 11 further comprising a miniaturized video camera including a lens and having an attached fiberoptic cable wherein said video camera is passed through said incision made in said patient's abdomen or chest and positioned adjacent an outer periphery of said first telescoping transparent tubular member in order to light an area of said patient's spine to be operated on and to transmit video images of said area.

13. A method of performing endoscopic or laparoscopic surgery on a patent's spine comprising the method steps of:

making an incision in said patient's abdomen or chest;

inserting a trochar which includes a first transparent tubular member of a predetermined diameter and a second transparent tubular member of a slightly greater diameter that slidingly accepts said first tubular member in a telescoping manner through said incision;

anchoring a pronged metal member threadingly placed on one end of said first transparent tubular member in to one of said patient's spine bones;

positioning a set screw and collar arrangement slidingly mounted on said second transparent tubular member against said patient's body so that a flanged end of said collar arrangement rests against said patient's body in order to stabilize said trochar in an upright position approximately perpendicular to said patient's body; and tightening a set screw threadingly mounted on said collar arrangement slidingly mounted on said second transparent tubular member to prevent further telescoping of said first and second transparent tubular members during surgery.

14. The method of claim 13 further comprising the method step of passing a miniaturized video camera with lens and fiberoptic cable through said incision to be positioned adjacent said first telescoping transparent tubular member.

15. The method of claim 14 further comprising the method step of turning on said miniaturized video camera to light an area of said patient's spine to be operated on.

16. The method of claim 15 further comprising the method step of transmitting video images of said area of said patient's spine being operated on to assist a surgeon viewing a screen of said video images in performing a particular surgical procedure on said patient's spine.

17. The method of claim 16 further comprising the method step of inserting surgical instruments through said first and second transparent telescoping tubes in order to perform said surgical procedure on said patient's spine.

18. The method step of claim 17 further comprising the method step of removing said trochar from said patient's body.

19. The method step of claim 18 further comprising the method step of suturing said incision in said patient's abdomen or chest in order to complete said surgical procedure.

* * * * *